United States Patent
Findly (12)

(10) Patent No.: US 6,617,440 B1
(45) Date of Patent: Sep. 9, 2003

(54) MYOSTATIN REGULATORY REGION, NUCLEOTIDE SEQUENCE DETERMINATION AND METHODS FOR ITS USE

(75) Inventor: Robert Craig Findly, Wethersfield, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/626,959

(22) Filed: Jul. 27, 2000

Related U.S. Application Data

(60) Provisional application No. 60/146,540, filed on Jul. 30, 1999.

(51) Int. Cl.[7] .................. C07H 21/04; C12N 15/74; C12N 5/02; C12N 15/09
(52) U.S. Cl. .................. 536/23.1; 536/24.1; 435/320.1; 435/325; 435/455
(58) Field of Search ................. 536/23.1, 24.1; 435/320.1, 325, 455

(56) References Cited

U.S. PATENT DOCUMENTS 6,284,882 B1 * 9/2001 Wu-Wong et al. ......... 536/24.1

FOREIGN PATENT DOCUMENTS

| WO | 9421681 | 9/1994 | |
|----|---------|--------|---|
| WO | 9833887 | 8/1998 | |
| WO | WO 9902667 A1 * | 1/1999 | C12N/5/00 |
| WO | 9942573 | 8/1999 | |
| WO | 0001810 | 1/2000 | |
| WO | 0004051 | 1/2000 | |

OTHER PUBLICATIONS

Sulston et al, Toward a complete human genome sequence, Genome Res 1998;8(11), 1097–1108.*
GenBank Accession No. A093798 reported Oct. 4, 1998.

* cited by examiner

*Primary Examiner*—Anne M. Wehbe'
*Assistant Examiner*—Q Janice Li
(74) *Attorney, Agent, or Firm*—Paul H. Ginsburg; Lorraine B. Ling; Kohn & Associates, PLLC

(57) ABSTRACT

The present invention relates to a transcription regulatory region of a myostatin gene. In particular, the invention relates to a 2.5 kb polynucleotide immediately 5' to the myostatin coding sequence, its nucleotide sequence and methods of using this regulatory region, and fragments thereof. The present invention relates to the use of the myostatin promoter of the present invention to direct expression of a target gene in a tissue specific manner, i.e. muscle tissue. The present invention relates to the use of the myostatin promoter of the present invention in high throughput screens to identify test compounds which inhibit myostatin promoter activity or myostatin expression. In accordance with the present invention, inhibitors of the myostatin promoter may be used to inhibit myostatin expression as a method of engineering animals with increased lean meat in order to decrease the time required to bring the animals to slaughter, and of promoting muscle growth for treating disorders related to expression of the myostatin gene, such as muscle wasting associated with aging or disease in humans and companion animals, particularly cats and dogs.

6 Claims, 4 Drawing Sheets

FIG. 1A

5'
AACCTTTTTAAGTCCTAAGTCACACGGAGTTCTATGTCCTCAAAATGTTGCTCAG
CCTCTACCCTGTCTACCCGGATGATTTTCTCTCCCAAACTGAGAGTCTGTAAACT
ATTAAGCATTAAGTACACACACCCTGACCCCAGCGGGCTCCATTCTCCATTC
TCCCCTGTGCTTAAAAGAAGCTGCCCTGAGTTTCAGTGCTATTATCAGAAAGC
AGCAGACAGCACGGCAGTTAAAAGCACAAGAAAGTAAATAACATGGTAATAA
ATAGGCAAAATAAAAGAAAATAAACAAGGAAATAAATAAAGGGCATTTGT
TCATAAAGTCAGAGCTGAGTGGCTGAGCTGGCAAACGCCCTCTGTCGTTATTATTATT
CTCAGTGGGAAATCTGGGTAGCTGGCAAACGCCCTCTGTCGTTATTATTATT
TTGCTGGCAATCTGAAACATGTAGGTGAGCTCAATTCCTAGGCCTAATGAGATG
TCCTTGCAGGTTGCGGAATCCCCTTGCCTTCATCTGAAGCACTTGAGGATAATTT
GAAAGTAAAAGGCTTGAAACAAAGAGCAAGCCCTTCTGCTTTCAAGTATTAATTA
CCTATGAAAGGGACTACATTAGCTACTTATATTGCTAAATTATATGCCTCAAAC
CCCTTTAGTTGAGAAATAAGATAAGAGAAGCTAAGTACTGTGCCGTCTTTGT
CATCGACTTAGAGAGGCAAAATTGAGATTGAACTCAGGTTTATTGACTCTT
CAGTCTCAGCTCACAATGGCAGTACAGTCTAAAAAAAAATCACAGGATC
AATTTCCTCTGAGGTATATAGCAGCATGTGTAATGATAATTATGACATCGAAAA
GAATTCTATGCAGAGAAATGAATTTCCAGACAAATCTGACTTTATAGCCTGCT
CTAATATTGTCTTGTATAAAGAGGGCCAGATCACCTCAGGTGTCTGCTTTGTG
TCTGGTTTCCTTCATCTTTAATGGTGGGCAAATCTAGTACATTATGGAAGCCCA
CTTTTTTTTCCTCAAGAGATATAGATGCCTCTTAAAATTTGATGAAATGCATT
AACTTTCAAGCTACTGAGCTGCATTTTAGTTCACTGAGGCAGTAAATTGGGTG
TATACTGTACAGAATGGTGGTGACCTAAAAATAAATATTTGATACAAGCACC
ATAGTCTCTTGGGGTGTGTGTAAGGGAGTAATGAATTAAAATTCTAAAGACTC
CTCAGCTTCCCAAACAGGAGGAGAACTCTGTGGCCTGGAAGCGTCCTCTGTC
CCTGCTGCTGTGTTGTTCAGCTCTTTAAGAGTTCACCCCATTCGATCTTGTGGC
TCCTAAAGCACCAAGGGTGAAAGTTTGATCCTTGCAGAGGCCACTTAAATTCAGAG
AACAAAAGCACCATTCTCTGCCCTAGACTCTAGCCCCAGATCCCTGCCAGGTGT
CTGCCTTCTGGTCAAAATGAGACGCTGGCAAAGGGGCTGGCAAAGGGGCTAGCCTGTGACAGT

FIG. 1B

ATGGGAACGCAACAAAGGACACCCCTCTACATGCGACTTGCTCTTTGTGTGCTC
ACGGACCTGACATCATTCACAGAGAACACAGATTGCACTTTACTGTCAGCCCT
GGAAGTCTGAGTCAAACTGAAATAATGCTCCAGCGCTACTTACAAAATCCATT
ATCTACTCGGCCTAAGTACAGAGCCTGGCCTCCTCGCTGACAGGATTCTGTTGG
CAATCAAAAAAAAAAAAAGCAACACTCAGTCTTTAGTCTGTATCTCT
GTAATAGAAATAGCAATACTTATAAGCTGAAATCAAGCACAGTTTTATGTTA
GTCAAAGCCATTAAGCTATCAAAAGTAAACCCATGTACACAGAAACGTCCCAGG
ACTGGTTTGTAATATGTCCTGACAAATAAGCCATGAAAACAAGCTCCTCAAATT
ACTGATGCAACTTTTTAGCAGGGTCACAAACTCAGCTTCTTTAAATTAAGTCAG
CTCTTCCTAGTTTTTACTTCTCTAATTACCCAGCACTTAACGCATATTTTTCCCT
CAAATATTAGTTTTAGTAACAAAATCTAAATTACTAACTTAAATGATAGCAAGA
TCTATTTAAACACAGAGATTAATAAGCTTTAAGTACAGTTTATATTAGTACACAGACTTCA
GTTTACAGAGATTAATAAGCTTTAAGTACAGTTTATATTAGTACACAGACTTCA
ATTTATCAAATGTCACATATCTTTCATGATTTGGGATTTATTTCATTTATGAA
GTAGTCAAGGGTTTAACCTCTGACTGTAACAAAATGCTGCTTGGTGACT
TGTGACAGACAGGGTTTAACCCTCTGACGACACTTGTCTCCTCTAAGTTGGAGCAGGAG
CCAATCATAGATCCTGACGACACTTGTCTCCTCTAAGTTGGAATATAAAAGCC
ACTTGGAATACAGTATACAGGACTCCCCTGGCGTGGCAGGTT

```
5' (2179)
Mur       AGATTAATAA GCTTTAAGTA CAGTTTATAT TA--GT--AC ACAGACTTCA ATTTATCAAA TGTCACATAT ATCTTTCATG ATTTGGGAT
Por       AGATTAATAA TATTTAAGTG CAGTTTATAT TATTGTTAAC ATAGATTTTA ATTTTTCAAA TGTCACATAT ATCTTTCATT ATTTGTAGAT
5' (1232)

Mur       TTATTTCATT TATGAAGTAG TCAAATGAAT CAGCTTGCCC TTGACTGTAA CAAAATGCTG CTTGGTGACT TGTGACAGAC AGGGTTTTAA
Por       TTATTTCTTT TATGAAGTAG TCAAATGAAT CAGCTCACCC TTGACTGTAA CAAAATACTG TTTGGTGACT TGTGACAGAC AGGGTTTTAA

Mur       CCTCTGACAG CGAGATTCAT TGTGGAGCAG GAGCCAATCA TAGATCCTGA CGACACTTGT CTCCTCTAAG TTGGAATATA AAAAGCCACT
Por       CCTCTGACAG CGAGATTCAT TGTGGAGCAA GAGCCAACTA TAGATCCTGA CGACACAGTTGT CTCATC-AAG -TGGAATATA AAAAGCCACT

Mur       TGGAATACAG TATACAGGAC TCCCTGGGGT GGCAAGTT    3' (2482)
Por       TGGAATACAG TATAAAAGAT TCACTGGTGT GGCAAGTT    3' (1537)
```

MYOSTATIN REGULATORY REGION, NUCLEOTIDE SEQUENCE DETERMINATION AND METHODS FOR ITS USE

This application claims the benefit of U.S. Provisional Application No. 60/146,540, filed Jul. 30, 1999, the entire contents of which is in incorporated by reference herein.

BACKGROUND OF THE INVENTION

The present invention relates to a regulatory region that controls expression of a gene. In particular, it relates to the nucleotide sequence of a 5' regulatory region and fragments thereof, which promote transcription of the myostatin gene, to be referred to herein as the myostatin gene promoter. In particular, it relates to the 5' regulatory region and fragments thereof, which promote transcription of the murine myostatin gene. The invention also relates to methods of using this region to regulate expression of a heterologous gene in cells or animals, to engineer host cells, to screen for compounds that activate or inhibit its transcription and expression, as well as methods of inhibiting its expression in cells for the promotion of muscle growth in livestock, poultry, fish and companion animals, as well as for the treatment of muscle wasting and neuromuscular diseases.

Growth and differentiation factor-8 (GDF-8 or myostatin), which will be referred to herein as myostatin, is a member of the transforming growth factor-β (TGF-β) superfamily of secreted growth and differentiation factors (McPherron, et al. *Nature* 387:83 (1997)). The members of the TGF-β family are synthesized as large precursor proteins that are proteolytically cleaved at a cluster of basic residues approximately 110–140 amino acids from the C-terminus. The C-terminal regions, which are active as disulfide-linked dimers, have some level of amino acid sequence and structural similarity. The TGF-β family is characterized by a consensus amino acid sequence and conserved cysteine residues involved in intrachain disulfide bonds that result in a cystine knot protein fold. Members of the family include Mullerian inhibitory substance (MIS) (Behringer, et al., 1990, Nature, 345:167), bone morphogenic proteins (BMPs) (Sampath, et al., 1990, J.Biol.Chem. 265:13198), growth and differentiation factors (GDFs), inhibins, and Drosophila decapentaplegic protein (DPP-C) (Padgett, et. al., 1987, Nature 325:81).

Myostatin has been identified in all vertebrates examined, including mouse, rat, human, baboon, cattle, pig, sheep, chicken, turkey, cats, dogs and fish. A disruption of the myostatin gene in mice leads to large increases in skeletal muscle mass resulting from muscle hyperplasia and hypertrophy and is at least partially responsible for the hyper-muscled phenotype of mice homozygous for the Cmpt (compact) mutation (McPherron et al. (1997); Szabo, G. et al. *Mammalian Genome* 9:671 (1998)). In double-muscled breeds of cattle such as the Belgian Blue or Piedmontese, the bovine myostatin gene has been shown to be partially deleted or contains a missense mutation. (Grobet, L. et al. *Nat. Genet.* 17:71 (1997); Kambadur, R. et al, *Genome Res.* 7:910 (1997); McPherron and Lee, *Proc. Natl. Acad. Sci USA* 94:12457 (1997)). Thus, myostatin seems to function as a negative regulator of skeletal muscle growth, however the mechanisms that regulate its expression have not been described (McPherron et al. (1997)).

The sequence of the cDNA for myostatin has been determined for each of these species and the deduced amino acid sequence is extraordinarily conserved, particularly the amino acid sequence of the C-terminal 109 amino acids. The nucleotide sequences of the full-length amino acid coding regions of the human and murine myostatin genes were disclosed in WO94/21681 to Lee and McPherron (1994). The nucleotide sequences of the full-length amino acid coding regions of the rat and chicken myostatin genes were disclosed in WO 98/33887 to Lee and McPherron (1998). While the coding sequences of the human and murine myostatin genes have been determined, those regulatory sequences which control expression of these genes remain uncharacterized.

SUMMARY OF THE INVENTION

The present invention relates to a transcription regulatory region of a myostatin gene. In particular, the invention relates to a 2.5 kb polynucleotide sequence immediately 5' to the murine myostatin coding sequence, its nucleotide sequence and methods of using this regulatory region, and fragments thereof. The present invention relates to the use of the myostatin promoter of the present invention to direct expression of a target gene in a cell or tissue specific manner, e.g., muscle cells or tissue. The present invention relates to the use of the myostatin promoter of the present invention in high throughput screens to identify test compounds which inhibit myostatin promoter activity or myostatin expression. The present invention relates to methods for increasing muscle mass and feed efficiency of livestock, poultry or fish, in particular to engineer animals with increased lean meat in order to decrease the time required to bring the animals to slaughter. In accordance with the present invention, inhibitors of the myostatin promoter may be used to inhibit myostatin expression as a method of treating disorders related to expression of the myostatin gene, such as muscle wasting associated with aging or disease in humans and companion animals.

The invention is based on the determination of the complete nucleotide sequence of the 2.5 kb murine myostatin gene promoter. Although the nucleotide sequence of the myostatin gene was previously reported, the myostatin promoter region has not yet been reported. Using a combination of manipulations, the promoter region of the murine myostatin gene was identified, sequenced and reported herein. When the 2.5 kb region and certain fragments thereof were placed upstream of a luciferase reporter gene in an expression vector, and introduced into muscle cell lines, these sequences induced the expression of the reporter gene. In addition, the identified promoter sequence of the murine myostatin gene and the identified promoter sequence of the porcine myostatin gene show a high degree of homology.

It is an object of the invention that the 2.5 kb regulatory region, or transcriptionally active fragments thereof be inserted in an expression vector to regulate the expression of a downstream coding sequence in a cell in vitro and in vivo.

In another embodiment of the invention, the aforementioned vector is stably integrated into the genome of a host cell. The cell is treated with a test compound in a screening assay for determining the ability of the compound to activate or inhibit the transcriptional activities of the regulatory region. The selected compounds may be formulated as pharmaceutical compositions for the promotion of muscle growth or for treatment of disorders related to aberrant expression of myostatin.

In yet another embodiment of the invention, the aforementioned vector is introduced into an embryonic cell or other type of cell, for the construction of a transgenic animal to regulate the expression of a transgene in a tissue specific manner.

It is also an object of the invention that polynucleotides complementary to the 2.5 Kb regulatory region or portions thereof be delivered to cells to inhibit the transcription activities of the endogenous 2.5 Kb region, thereby down-regulating the expression of myostatin. Such polynucleotides are useful for the promotion of growth, or in the treatment of diseases associated with myostatin expression, such as muscle wasting and neuromuscular disease.

The present invention also relates to methods of treating livestock, poultry or fish to promote muscle growth. In particular, the invention relates to methods for increasing muscle mass and feed efficiency in order to increase growth so that animals can be brought to slaughter sooner. The methods of treatment of the present invention are applicable to humans and non-humans.

The invention further relates to methods for the treatment of disorders, such as muscle wasting, neuromuscular disease, cancer and aging, wherein such methods comprise administering compounds which modulate the expression of a myostatin gene so symptoms of the disorder are ameliorated.

In addition, the present invention is directed to methods that utilize the myostatin promoter sequences for the diagnostic evaluation, genetic testing and prognosis of a disease or disorder associated with myostatin expression.

The invention still further relates to methods of identifying compounds capable of modulating the activity of myostatin promoters and the expression of myostatin genes, wherein such methods comprise administering a compound to a cell that expresses a gene under the control of a myostatin promoter or a transcriptionally active fragment thereof, measuring the level of gene expression or gene product activity and comparing this level to the level of gene expression or gene product activity produced by the cell in the absence of the compound, such that if the level obtained in the presence of the compound differs from that obtained in its absence, a compound capable of modulating the expression of the myostatin gene or promoter activity has been identified.

BRIEF DESCRIPTION OF THE DRAWINGS

FIGS. 1A–1B: DNA sequence (SEQ ID NO: 1) of 2482 bp upstream of the murine myostatin gene coding region. This DNA sequence includes part of the murine myostatin promoter region that controls expression of the myostatin gene.

FIG. 3: Comparison of DNA sequence homology between regions of the murine (SEQ ID NO: 1) and porcine (SEQ ID NO: 2; Accession number AF093798) myostatin promoters proximal to the transcription start sites of those genes.

DETAILED DESCRIPTION OF THE INVENTION

Figure 2:
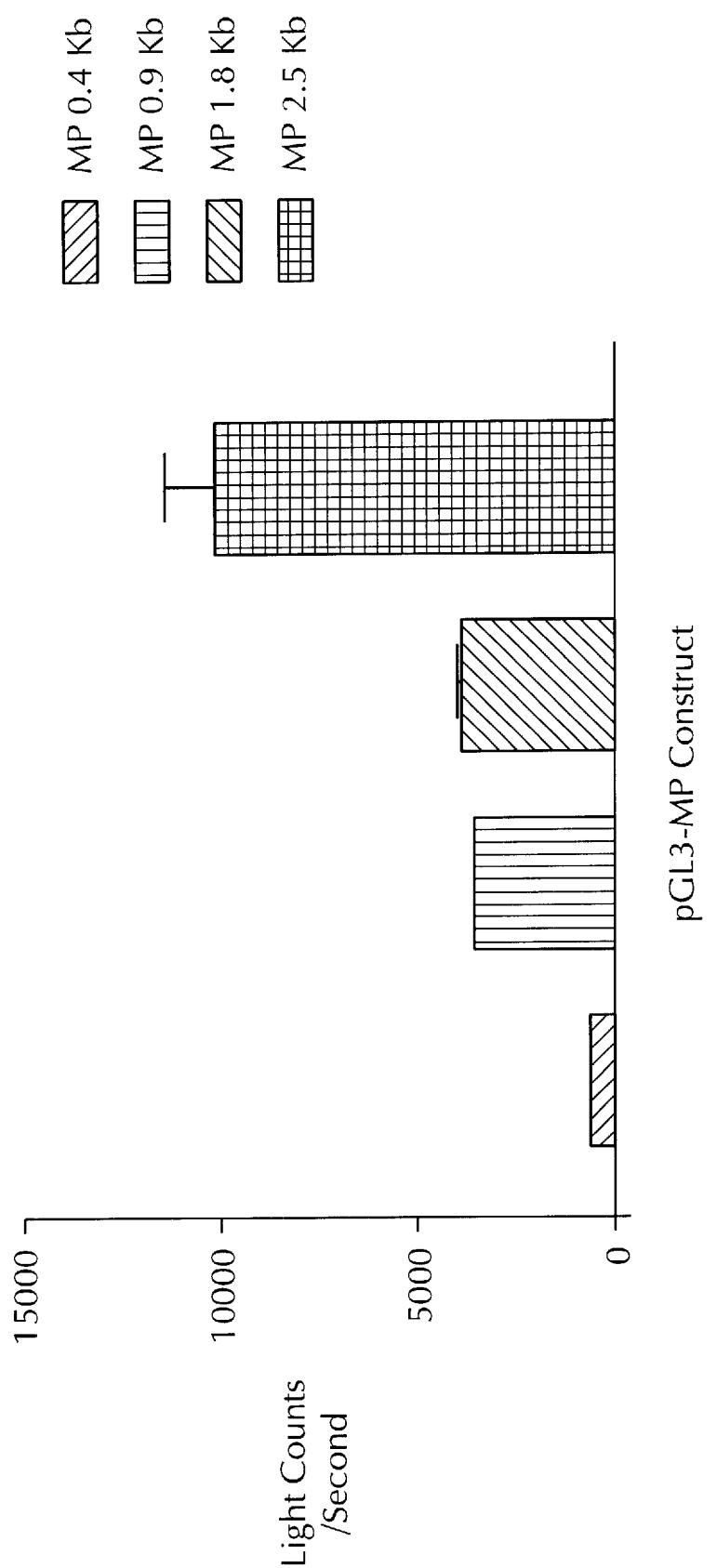
FIG. 2: The efficiency of four murine myostatin promoter DNA fragments to direct expression of luciferase was measured using the Luciferase Assay System (Promega).

The present invention relates to a polynucleotide sequence encoding an element of a myostatin gene that promotes transcription. In particular, the present invention relates to a polynucleotide of 2482 nucleotides (or 2.5 kb fragment) that is located immediately 5' to the transcription start site of the murine myostatin gene. Also encompassed within the scope of the invention are various fragments of this regulatory region that promote transcription. In one embodiment of the invention, the regulatory region is a 1.8 kb fragment containing a deletion of up to 0.7 Kb at the 5' end of the promoter sequence. In another embodiment of the invention, the regulatory region comprises DNA binding sites for various transcription factors, including but not limited to, GATA and ATF-CREB.

The myostatin promoter region of the present invention is preferably derived from a mammalian organism, and most preferably human, mouse, rat, cow, pig, sheep or companion animals, particularly cats and dogs. The myostatin promoter region may also be derived from chicken, turkey, fish and other species described herein.

The myostatin promoter region of the present invention and active fragments thereof can be used to direct the expression of a heterologous coding sequence. In particular, the present invention encompasses human, murine, bovine, avian, canine, feline and porcine species of the myostatin promoter region. In accordance with the present invention, active fragments of the myostatin promoter region encompass those fragments of the promoter which are of sufficient length to promote transcription of a coding sequence to which the fragment is operatively linked. In particular, the active fragments of the myostatin promoter of the present invention encompass those fragments that are of sufficient length to promote transcription of a luciferase promoter gene when operatively linked to the luciferase coding sequence and transfected into a muscle cell line. Typically, the coding sequence is placed immediately 3' to and is operatively linked to the promoter region. The nucleotide sequence of this region is shown in FIGS. 1A–B (SEQ ID NO: 1). The sequence shown represents only one strand of the functional promoter, which is double stranded. Also encompassed within the scope of the invention are modifications of this nucleotide sequence that do not substantially affect its transcriptional activities. Such modifications include additions, deletions and substitutions. In addition, any nucleotide sequence that selectively hybridizes to the sequence of SEQ ID NO: 1 under stringent conditions, and is capable of activating the expression of a coding sequence is encompassed by the invention. When placed upstream of the coding region for a heterologous gene, as discussed in more detail below, the 2482 bp fragment (from nucleotide 1 to 2482) is sufficient to direct expression of a luciferase reporter gene, or porcine growth hormone releasing hormone, when transfected into a murine C2C12 cell line. Exemplary stringent hybridization conditions are as follows: pre-hybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, and 0.02% BSA. Filters are hybridized for 48 hours at 65° C. in pre-hybridization mixture containing radioactive or chemically labeled probes. Washing of filters is done at 37° C. for 1 hour in several changes of a solution containing 2×SSC, 0.01% PVP, 0.01% Ficoll, and 0.01% BSA before autoradiography. Other conditions of high stringency which may be used are well known in the art. For example, see, Sambrook, et al (Eds.), 1989, *Molecular Cloning: A Laboratory Manual*, Cold Spring Harbor Laboratory of Press Inc, Plainview, N.Y.; Ausubel et al., (Eds.) 1998, *Current Protocols in Molecular Biology*, John Wiley and Sons, Inc, New York; each of which is incorporated herein by reference in its entirety.

The present invention also relates to the determination of regions of high homology or identity between the myostatin promoter regions derived from different species. In particular, the nucleotide sequence of the murine myostatin promoter region (SEQ ID NO: 1) was compared to the porcine promoter sequence (SEQ ID NO: 2), see FIG. 3. The area of greatest homology is the 90% sequence homology between the murine and porcine myostatin promoter at position 2178 to 2482 of the murine promoter sequence (SEQ ID NO. 3). Thus, in one aspect, the present invention relates to the identification of the myostatin promoter region in other species based on complementarity to regions of the murine myostatin promoter at position 2178 to 2482 (SEQ ID NO. 3). This can be determined by hybridization assays as described herein. The present invention further relates to isolated nucleotide sequences which hybridize under stringent conditions to SEQ ID NO. 3 and are of sufficient length to promote transcription of a coding sequence to which the nucleotide sequence is operatively linked in a muscle cell of the same species that the nucleotide sequence is derived from, with the proviso that said nucleotide sequence is not derived from the porcine genome.

The myostatin promoter region, or transcriptionally active fragments thereof, is preferably derived from a mammalian organism, and most preferably from mouse, rat, cow, human or companion animals, particularly cats and dogs. The myostatin promoter region of the present invention may also be derived from chicken, turkey, fish and other species described herein. If regions of high homology of the myostatin regulatory region were identified among species, it would be routine for one of skill in the art to obtain promoter regions from any species using oligonucleotide probes that correspond to a part of the sequence encoding the myostatin promoter region in question. Additional methods, known to those of skill in the art, may also be employed to obtain the myostatin promoter region or transcriptionally active fragment thereof. Further, a mammalian myostatin promoter homologue may possibly be isolated from, for example, human nucleic acid, by performing PCR using two primer pools designed on the basis of the nucleotide sequence of the murine or porcine myostatin promoter disclosed herein. The template for the reaction is chromosomal DNA. For guidance regarding such conditions, see, for example, Innis et al. (Eds.) 1995, *PCR Strategies*, Academic Press Inc., San Diego; and Erlich (ed) 1992, *PCR Technology*, Oxford University Press, New York, each of which is incorporated herein by reference in its entirety.

The myostatin promoter regions and fragments thereof which promote transcription, and the fragments and probes described herein which serve to identify myostatin promoter regions and fragments thereof, may be produced by recombinant DNA technology using techniques well known in the art. Methods which are well known to those skilled in the art can be used to construct these sequences, either in isolated form or contained in expression vectors. These methods include, for example, in vitro recombinant DNA techniques, synthetic techniques and in vivo genetic recombination. See, for example, the techniques described Sambrook et al., 1989, supra, and Ausabel et al., 1998, supra; also see the techniques described in "Oligonucleotide Synthesis", 1984, Gait M. J. ed., IRL Press, Oxford, which is incorporated herein by reference in its entirety.

Alterations in the regulatory sequences can be generated using a variety of chemical and enzymatic methods which are well known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for increased periods of time (See Ausubel, et al., 1998 Current Protocols in Molecular Biology, for a review of mutagenesis techniques).

The altered sequences are evaluated for their ability to direct expression of heterologous coding sequences in appropriate host cells. Within the scope of the present invention are any altered regulatory sequences which retain their ability to direct expression of a coding sequence. In addition, such altered regulatory sequences can be incorporated into recombinant expression vectors for further use.

A wide variety of heterologous genes can be expressed under the control of the regulatory sequences of the present invention such as genes encoding vaccines, antigens, toxic gene products, potentially toxic gene products, and antiproliferation or cytostatic gene products. Reporter genes can also be expressed including enzymes, (e.g. CAT, beta-galactosidase, luciferase), fluorescent proteins such as green fluorescent protein, or antigenic markers.

The murine myostatin gene promoter region shows selective tissue specificity. It primarily induces gene expression in skeletal muscle cells, adipose cells, and in cells of the lactating mammary gland, but not in, for example, lung tissue. Thus, the regulatory region and transcriptionally active fragments thereof of the present invention may be used to induce expression of a heterologous gene in skeletal muscle cells. The present invention relates to the use of the myostatin gene promoter region to achieve tissue specific expression of a target gene for the promotion of growth or treatment of disease. In particular, the myostatin gene promoter region may be used to achieve tissue specific expression in gene therapy protocols. In cases where such cells are tumor cells, the induction of a cytotoxic product by the murine myostatin gene promoter region may be used in the form of cancer gene therapy. Additionally, antisense, antigene, or aptameric oligonucleotides may be delivered to cells using the presently described expression constructs. Ribozymes or single-stranded RNA can also be expressed in a cell to inhibit the expression of a particular gene of interest. The target genes for these antisense or ribozyme molecules should be those encoding gene products that are essential for cell maintenance.

Regardless of the choice of target sequence, it is preferred that in vitro studies are first performed to quantitate the ability of the oligonucleotide to inhibit gene expression. These studies should utilize controls that distinguish between specific inhibition and nonspecific biological effects of oligonucleotides. It is also preferred that these studies compare levels of the target RNA or protein with that of an internal control RNA or protein.

The myostatin gene promoter region disclosed herein may be inserted in a variety of expression vectors for introduction into host cells. In a preferred embodiment, the expression vector is stably integrated into the cell genome.

In mammalian host cells, a number of commercially available vectors can be engineered to insert the regulatory region of the invention (eg, Clontech, Palo Alto, Calif.).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, HEK 293, WI38, and the like.

The expression vectors that contain the murine myostatin gene promoter region may contain a gene encoding a selectable marker. A number of selection systems may be used, including but not limited to, the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. USA* 48:2026), or adenine phosphoribosyltransferase (Lowy, et al., 1980, *Cell* 22:817) genes, which can be employed in tk$^-$, hgprt$^{31}$ or aprt$^-$ cells, respectively. Also, anti-metabolite resistance can be used as the basis of selection for dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); or hygro, which confers resistance to hygromycin (Santerre, et al., 1984, *Gene* 30:147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, Current Communications in Molecular Biology, Cold Spring Harbor Laboratory ed.) and glutamine synthetase (Bebbington et al., 1992, Biotech 10:169).

The present invention also encompasses screening assays designed to identify compounds that modulate myostatin promoter activity or myostatin expression. The present invention encompasses in vitro cell-based assays. Compounds to be tested may include, but are not limited to, oligonucleotides, peptides, proteins, small organic or inorganic compounds, natural products, antibodies, etc. Combinatorial chemistry libraries can also be screened.

In a specific embodiment of the invention, the genetically-engineered cell lines of the present invention may be used to screen for small organic molecules, peptides, natural or synthetic compounds or other cell bound or soluble molecules that cause stimulation or inhibition of murine myostatin promoter transcriptional activities. Such compounds may be used to control skeletal muscle mass, thereby increasing performance and growth of livestock, poultry and fish. The present invention also encompasses methods to treat disorders related to reduced skeletal muscle mass, thereby treating muscle wasting associated with diseases such as amyotrophic lateral sclerosis, or by aging.

Random peptide libraries consisting of all possible combinations of amino acids attached to a solid phase support may be used to identify peptides that are able to activate or inhibit myostatin promoter activities (Lam, K. S. et al., 1991, *Nature* 354: 82–84). The screening of peptide libraries may have therapeutic value in the discovery of pharmaceutical agents that stimulate or inhibit the expression of myostatin by interaction with the promoter region.

The assays of the present invention relate to identifying compounds capable of modulating the activity of a myostatin promoter and the expression of a myostatin gene, wherein such methods comprise administering a compound to a cell line that expresses a gene under the control of a myostatin promoter or a fragment thereof, which promotes transcription, measuring the level of gene expression or gene product activity and comparing this level to the level of gene expression or gene product activity produced by the cell line in the absence of the compound, such that if the level obtained in the presence of the compound differs from that obtained in its absence, a compound capable of modulating the expression of the mammalian myostatin gene or promoter activity is identified. Alterations in gene expression levels may be measured by any number of methods known to those of skill in the art e.g., by assaying all lysates for mRNA transcripts by Northern analysis, or by assaying for gene products expressed by the reporter gene.

An example of such an in vitro screening assay is described below. The 2.5 kb promoter luciferase reporter vector is used to establish a stable cell line in murine C2C12 muscle cells. The C2C12 cell line is plated in 96-well plates using medium appropriate for the cell line. Potential inhibitors of myostatin gene expression are added to the cells. The effect of the inhibitors of myostatin gene activation can be determined by measuring the response of the luciferase reporter gene driven by the myostatin promoter. This assay is easily set up in a high-throughput screening mode for evaluation of compound libraries in a 96-well format that reduce (or increase) luciferase activity. For example, C2C12 cells (ATCC #CRL-1772) stably transfected with the 2.5 kb promoter-luciferase reporter gene construct are plated in 96-well tissue culture plates and grown in DMEM, 10% fetal bovine serum at 37° C., 5% $CO_2$ for 18 hours. Test compounds are then added, cells grown for an additional 48 hours, and the cells are lysed by freezing and thawing in Cell Culture Lysis Reagent (Promega). Luciferase activity is determined by adding Luciferase Assay Substrate and Buffer (Promega) to the suspension of lysed cells, and relative light units are determined using a Wallac 1450 Microbeta counter.

Once a compound has been identified that inhibits myostatin promoter activity, it may then be tested in an animal-based assay to determine if the compound exhibits the ability to promote muscle mass and/or muscle growth or to ameliorate symptoms, such as muscle wasting, neuromuscular disorders, or aging.

The mammalian myostatin regulatory region can be used to direct expression of a coding sequence in animals by transgenic technology. Animals of any species, including, but not limited to, mice, rats, rabbits, guinea pigs, pigs, micro-pigs, goats, sheep, cattle, chickens, fish and non-human primates, e.g., baboons, monkeys and chimpanzees may be used to generate transgenic animals. The term "transgenic", as used herein, refers to animals expressing coding sequences from a different species (e.g., mice expressing human gene sequences), as well as animals that have been genetically engineered to no longer express endogenous gene sequences (i.e., "knock-out" animals). In transgenic animals that express coding sequences from a different species, as well as in the genetically engineered "knock out" transgenic animals, the altered coding sequences are present in a stably integrated form in their somatic cells, and may also be stably integrated into their germ cell lines so that the altered coding sequences are passed on to their progeny. The present invention encompasses transgenic animals whose progeny contain such stably integrated altered coding sequences as well as transgenic animals wherein the altered coding sequences are stably integrated only in their somatic cells, and therefore not passed on to their progeny. As used herein, "progeny" also refers to subsequent generations of single cells.

The present invention encompasses non-human transgenic animals which are useful as a source of food products with high muscle and protein content, and reduced fat and cholesterol content. The animals have been altered chromosomally in their germ cells and somatic cells so that the myostatin gene is expressed at lower amounts or is completely disrupted, resulting in animals with decreased levels of myostatin and higher than normal levels of muscle tissue, preferably without increased fat and/or cholesterol levels.

Any technique known in the art may be used to introduce a transgene under the control of myostatin regulatory region into animals to produce the founder lines of transgenic animals. Such techniques include, but are not limited to, pronuclear microinjection (Hoppe & Wagner, 1989, U.S. Pat. No. 4,873,191); retrovirus gene transfer into germ lines (Van der Putten et al., 1985, Proc. Natl. Acad. Sci., USA 82:6148–6152); gene targeting in embryonic stem cells (Thompson et al., 1989, Cell 65:313–321); electroporation of embryos (Lo, 1983, Mol. Cell. Biol. 31:1803–1814); and sperm-mediated gene transfer (Lavitrano et al., 1989, Cell 57:717–723) (see, Gordon, 1989, Transgenic Animals, Intl. Rev. Cytol. 115:171–229).

Any technique known in the art may be used to produce transgenic animal clones containing a transgene, for example, nuclear transfer into enucleated oocytes of nuclei from transgenic animals, or from cultured embryonic, fetal or adult cells (Campbell, et al., 1996, Nature 380:64–66; Wilmut, et al., Nature 385:810–813).

The present invention provides for transgenic animals that carry a transgene such as a reporter gene under the control of the myostatin regulatory region or fragments thereof that can promote transcription in all their cells, as well as animals that carry the transgene in some, but not all of their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (1992, Proc. Natl. Acad. Sci. USA 89:6232–6236). When it is desired that the transgene be integrated into the chromosomal site of the endogenous corresponding gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene.

Once transgenic animals have been generated, the transcriptional activities of the myostatin regulatory region may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of transgene-expressing tissue, may also be evaluated immunocytochemically using antibodies specific for the transgene product. Such animals may be used as in vivo systems for the screening of agents that activate or inhibit myostatin activities.

The myostatin promoter region and fragments thereof of the present invention that promote transcription may be used for a wide variety of purposes, e.g., to achieve tissue specific expression or to down regulate gene expression.

The endogenous myostatin promoter region may be targeted to specifically down-regulate myostatin gene expression. For example, oligonucleotides complementary to the regulatory region may be designed and delivered to the cells that overproduce myostatin. Such oligonucleotides anneal to the regulatory sequence, and prevent transcription activation. Alternatively, the regulatory sequence or portions thereof may be delivered to cells in saturating concentrations to compete for transcription factor binding. For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215. Methods commonly known in the art of recombinant DNA technology which can be used are described in Ausubel et al. (eds.), 1998, Current Protocols in Molecular Biology, John Wiley & Sons, NY; and Kriegler, 1990, Gene Transfer and Expression, A Laboratory Manual, Stockton Press, NY.

In a specific embodiment, the nucleic acid is directly introduced into a target cell in vivo. By "introduced into," as used herein, means administered to, or allowed to enter into, a target cell. This can be accomplished by any methods known in the art, e.g., by constructing the nucleic acid as part of an appropriate nucleic acid expression vector and introducing it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by introducing it in linkage to a peptide which is known to enter the nucleus, or by introducing it in linkage to a ligand subject to receptor-mediated endocytosis (see e.g., Wu and Wu, 1987, J. Biol. Chem. 262:4429–4432), which can be used to target cell types specifically expressing the receptors. As used herein, a "target cell" can be a type of cell or tissue in an organism, or a single cell type, e.g., grown in tissue culture. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijistra et al., 1989, Nature 342:435–438).

The oligonucleotide may comprise at least one modified base moiety which is selected from the group including, but not limited to: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5N-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

Endogenous target gene expression can also be reduced by inactivating or "knocking out" the myostatin regulatory region using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, DNA that contains in part, a fragment homologous to the promoter region of the myostatin gene can be used, with or without a selectable marker, to transfect cells. Insertion of the DNA construct, via targeted homologous recombination, results in inactivation of the myostatin promoter.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Triple helix molecules may be prepared by any method known in the art for the synthesis of nucleic acid molecules. These include techniques for chemically synthesizing oligonucleotides well known in the art such as, for example, using N-phosphonate or phosphoramidite chemistries (Froehler et al., 1986, *Nucleic Acid Res.* 14:5399–5407; McBride et al., 1983, *Tetrahedron Lett.* 24:246–248).

In addition, peptide nucleic acid chimeras can be used to inhibit the expression of specific genes (Uhlmann, 1998, Biological Chem. 379:1045).

The anti-sense RNA and DNA molecules and triple helix molecules of the invention may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phospho-diesterase linkages within the oligodeoxyribonucleotide backbone.

The myostatin promoter region and fragments thereof that promote transcription of the present invention can also be used to achieve tissue specific expression of a target gene. Thus, it is possible to design appropriate therapeutic techniques directed to this regulatory sequence in order to modulate the expression of a target gene. In accordance with the present invention, the term "modulate" encompasses the suppression or augmentation of expression of a target gene and also encompasses the tissue specific suppression or expression of a target gene. When a cell proliferative disorder is associated with underexpression or overexpression of a myostatin gene product, small organic molecules or oligonucleotide-based compounds such as those described herein, including antisense oligonucleotides, may be used to modulate expression of the myostatin gene. Such muscle associated disorders may encompass cancer, muscular dystrophy, spinal cord injury, neurodegenerative disorders, traumatic injury, congestive obstructive pulmonary disease (COPD), AIDS, cachecia, or aging. In accordance with the present invention, the myostatin regulatory element of the present invention may be used to achieve muscle specific expression of a target gene to promote muscle growth and increase muscle mass for the treatment of a muscle associated disorder. For example, in cases where the muscle associated disorder is cancer, the expression of a cytotoxic gene product under the regulation of the myostatin gene promoter may be used as a cancer therapy. One of skill in the art can determine if a particular therapeutic course of treatment is successful by several methods known to those of skill in the art, including muscle fiber analysis or biopsy.

The present invention also encompasses utilizing the myostatin promoter region to modulate the expression of the myostatin gene as a method of producing animal food products having increased muscle and protein content, and reduced fat and cholesterol content. Organic molecules or oligonucleotide-based compounds as described herein that directly or indirectly regulate the expression of the myostatin region may be used to reduce expression of the myostatin gene product. Such organic molecules, including but not limited to small organic molecules, or oligonucleotide-based compounds that directly or indirectly regulate expression of the myostatin promoter may be administered to a livestock animal, including but not limited to cattle, sheep, pig, turkey, chicken, and fish, or to companion animals, particularly cats and dogs, to result in the decreased expression of myostatin in the animal and consequent higher than normal levels of muscle tissue, preferably without increased fat and/or cholesterol levels.

EXAMPLE 1

Determination of the Nucleotide Sequence of the Murine Myostatin Promoter Region and Effects of Various Fragments of the Region in Transcription Activation Materials and Methods C2C12 are murine muscle cell lines (ATCC #CRL-1772). These cells were maintained in standard culture media at 37° C.

The murine myostatin promoter was cloned by PCR using a commercial murine genomic library kit (GenomeWalker Kit, Clontech). Murine genomic DNA was digested with a restriction enzyme to produce large DNA fragments and PCR adaptors were ligated onto both ends of the DNA fragments. Nested PCR reactions were performed using a forward primer homologous with a sequence near the 5' end of the published myostatin coding region as the initial primer and a reverse primer that recognized a Clontech PCR adaptor. This was followed by a second PCR reaction using a forward primer that included 23 bases of the myostatin untranslated leader sequence and a second Clontech adaptor. These reactions yielded a product that included 23 bases of the 5' untranslated myostatin mRNA and 1792 bases of promoter sequence (1.8 Kb).

Subsequently, a new primer was designed based on sequence near the 5' end of the 1.8 Kb promoter sequence and a second PCR reaction was performed using the Genome Walker kit. This yielded a 930 bp PCR product which overlapped the 5' end of the original 1.8 kb promoter. When the two PCR products were combined by cloning into a single fragment, a 2482 bp promoter fragment (2.5 Kb) was obtained.

The 1.8 kb and 2.5 kb myostatin promoter fragments and additional subclones of 320 bp and 901 bp proximal to the myostatin protein coding region were placed into the multicloning site of the pGL3 basic vector (Promega) 5' to the coding sequence for luciferase. In this vector, the luciferase gene lacks a promoter, and, consequently, is under the control of any promoter cloned upstream of it. These plasmid vectors were used to transiently transfect C2C12 cells, using Fugene (Boehringer Mannheim) as a carrier to introduce the plasmid into the cells. The cell cultures were grown at 37° C., 5% CO2, in DMEM, and luciferase activity was measured using a commercial kit (Promega Luciferase Assay System, E150).

The 1.8 Kb, 930 bp, and 2482 bp clones of the promoter were sequenced. The nucleotide sequence of the 2482 bp fragment of the murine myostatin promoter is depicted in FIGS. 1A–B (SEQ ID NO. 1), with the nucleotide labeled 2482 being the first base 5' to the published sequence of the murine myostatin gene.

The two primers specific to the published myostatin sequence used to generate the 1.8 kb clone of the promoter were: 5' ACTGGGCCAGCAGCAATCAG 3' (SEQ ID NO: 4) and 5' GAGTAATGCCAAGTGAAATA 3' (SEQ ID NO: 5) (nested primer).

The two primers specific to the 1.8 kb promoter sequence used to clone the 930 bp fragment were: 5' GCAGACAC-CCTGAGGTGATCTGGCCCTCT 3' (SEQ ID NO: 6) and 5' TTTTCTGCATAGAATTCTTTTCGATGTC 3' (SEQ ID NO: 7) (nested primer).

In both cases, the two primers specific to the ligated adaptor and supplied by Clontech were: 5' GTAATAC-GACTCACTATAGGGC 3' (SEQ ID NO: 8) and 5' ACT-ATAGGGCACGCGTGGT 3' (SEQ ID NO: 9).

Results

The ability of the various fragments of the murine myostatin promoter region to control expression of the luciferase reporter gene in transient transfection assays is shown in FIG. 2. In each experiment, C2C12 cells were co-transfected with a second vector that employs a CMV promotor to express constitutively a Renilla luciferase gene (pRL-CMV, Promega). Values presented for the myostatin promoter constructs were all normalized against Renilla luciferase activity. The 0.4 kb promoter fragment showed little transcriptional activity, the 0.9 kb fragment had 35% of the activity of the 2.5 kb fragment, and the 1.8 kb fragment had 39% of the activity of the 2.5 kb fragment. These results demonstrate that the 2.5 kb fragment is the strongest promoter of those tested.

Initial DNA homology searches of GenBank did not reveal any sequences with homology to the 2.5 kb myostatin promoter sequence, demonstrating to the best of applicants knowledge the first identification of the murine promoter sequence. The sequence of 1673 bases of the porcine myostatin promoter was reported in GenBank (Accession number AF093798, reported Oct. 4, 1998). The murine and porcine promoters show significant homology. When the porcine sequence is aligned with the murine promoter sequence a highly homologous region is identified 5' to base 1537 of the published porcine myostatin promoter sequence. In particular, the two sequences are 89% homologous over the region of 2179 to 2482 of the murine promoter, corresponding to bases 1232 to 1537 of the published porcine sequence (FIG. 3), and continue to share regions of homology through the rest of the promoter sequences. However, the deposited porcine myostatin promoter sequence is only 1673 bases and includes mRNA sequence of the myostatin gene. This is less than the 2482 bases of the murine promoter, which has been shown to be crucial for efficient in vitro gene expression. This suggests that the murine myostatin promoter would be a more effective promoter for use in experiments on in vitro expression than the porcine myostatin promoter.

EXAMPLE 2

High Throughput Screening Assays to Identify Regulators of Myostatin Promoter Activity C2C12 cells, obtained from ATCC, were co-transfected with the myostatin promoter-luciferase reporter plasmid and a second plasmid (pcDNA3, Invitrogen) expressing aminoglycoside phosphotransferase, which confers resistance to the antibiotic geneticin (G418). C2C12 cells were selected in 800 μg/mL of G418, individual colonies were picked and replated at low dilution, and individual colonies were again isolated by selection in GH18. Cell lines established from these colonies express luciferase, and those with the lowest number of introduced copies of the myostatin promoter luciferase reporter construct were selected for use in high throughput screens.

In order to identify compounds that modulate myostatin promoter activity, the following assay may be conducted. Stably transfected cells are plated in 96-well plates using medium appropriate for the cell line. Potential inhibitors of myostatin gene expression are added to the cells. The effect of the inhibitors of myostatin gene activation can be determined by measuring the response of the luciferase reporter gene driven by the myostatin promoter. This assay can be set up in a high-throughput screening mode for evaluation of compound libraries that reduce (or increase) luciferase activity. For example, C2C12 cells (ATCC #CRL-1772) stably transfected with the 2.5 kb promoter-luciferase reporter gene construct are plated at 3,000 cells per well in 96 well tissue culture plates and grown in DMEM, 10% fetal bovine serum at 37° C., 5% $CO_2$ for 18 hours. Test compounds are then added, cells grown for an additional 48 hours, and the cells are lysed by freezing and thawing in Cell Culture Lysis Reagent (Promega). Luciferase activity is determined by adding Luciferase Assay Substrate and Buffer (Promega) to the suspension of lysed cells, and relative light units determined using a Wallac 1450 Microbeta counter. The cytotoxicty of test compounds is determined using the tetrazolium salt WST-1 in a colorimetric assay for cell viability. Preferred compounds with inhibit expression of the myostatin promoter luciferase reporter gene construct, and will be nontoxic.

Expression of Muscle-specific Genes Using Naked Dna Expression

Direct injection into muscle of DNA plasmids with muscle specific or constitutive promoters results in expression of the gene under control of that promoter. A vector utilizing the murine 2.5 kb myostatin promoter to drive expression of porcine growth hormone releasing hormone (GHRH) was constructed. When this vector was transiently transfected into C2C12 muscle cells, expression of GHRH could be detected in culture supernatants at levels similar to those found using a CMV promoter. In accordance with the present invention, the construct may be directly introduced into a host by direct injection of naked DNA.

The present invention is not to be limited in scope by the exemplified embodiments which are intended as illustrations of single aspects of the invention, and any clones, or nucleotide sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. An isolated polynucleotide comprising the nucleotide sequence of SEQ ID NO: 1 from 1 to 2482 (2.5 kb fragment) that promotes transcription.

2. A recombinant vector comprising the polynucleotide of claim 1.

3. A recombinant expression vector comprising the polynucleotide of claim 1 in which the nucleotide sequence of the polynucleotide is operably associated with a coding sequence.

4. A genetically engineered host cell comprising the vector of claim 2 or 3.

5. The host cell of claim 4 in which the coding sequence is a reporter gene.

6. The host cell of claim 5 in which the reporter gene is luciferase.

* * * * *

UNITED STATES PATENT AND TRADEMARK OFFICE
CERTIFICATE OF CORRECTION

PATENT NO. : 6,617,440 B1
DATED : September 9, 2003
INVENTOR(S) : Findly

It is certified that error appears in the above-identified patent and that said Letters Patent is hereby corrected as shown below:

Title page,
Item [*] Notice, delete the phrase "by 0 days" an insert -- by 261 days --

Signed and Sealed this

Nineteenth Day of April, 2005

JON W. DUDAS
*Director of the United States Patent and Trademark Office*

SEQUENCE LISTING

<160> NUMBER OF SEQ ID NOS: 9

<210> SEQ ID NO 1
<211> LENGTH: 2482
<212> TYPE: DNA
<213> ORGANISM: Mus musculus

<400> SEQUENCE: 1

```
aacctttta agtcctaagt cacacggagt tctatgtcct caaaatgttg ctcagcctct      60
accctgtcta cccggatgat tttctctccc aaactgagag tctgtaaact attaagcatt     120
aagtacacac acaccctgac cccagcgggc tccattctcc attctcccct gtgcttaaaa     180
gaagctgccc tggagtttca gtgctattat cagaaagcag cagacagcac gggcagttaa     240
aagcacaaga aagtaaataa catggtaata aataggcaaa ataaagaaa ataaacaaac      300 aaggaaataa ataaagggca tttgttcata aagtcagagc tgagtgaatg gctcaggctt     360
tgccctgccc tgcccaagct cagtgggaaa tctgggtagc tggcaaacgc ctctgtcgtc     420
gttattatta ttttgctggc aatctgaaac atgtaggtga gctcaattcc taggcctaat     480
gagatgtcct tgcaggttgc ggaatccctt gccttcatct gaagcacttg aggataattt     540
gaaagtaaaa ggcttgaaac aaagagcaag cccttctgct tcaagtatta attacctatg     600
aaagggacta catttagcta cttatattgc taaattatat gcctcaaacc cctttagttg     660
agaaactaaa gataagagaa gctaagtact gtgccgtctt tgtcatcgac ttagaagagg     720
caaaattgag atttgaactc aggtttattt gactcttcag tctcagctca caatggcagt     780
acagtctaaa aaaaaaaaaa atcacaggat caatttcctc tgaggtatat agcagcatgt     840
gtaatgataa ttatgacatc gaaagaatt ctatgcagaa aaatgaattt tccagacaaa      900
tctgacttta taggcctgct ctaatattgt cttgtataaa gagggccaga tcacctcagg     960
gtgtctgctt tgtgtctggt tttccttcat ctttaatggt gggcaaatct agtacattat    1020
ggaagcccac tttttttttc ctcaagagat atagatgcct cttaaaaatt tgatgaaaat    1080
gcattaactt ttcaagctac tgagctgcat tttagttcac tgaggcagta aattgggtgt    1140
atactgtaca ggaatggtgg tgacctaaaa ataaatattt gatacaagcc accatagtct    1200
```

-continued

| | |
|---|---|
| cttggggtgt gtgtaagggg agtaatgaat taaaattcta aagactcctc agcttcccaa | 1260 |
| acaggaggag gaactctgtg gcctggaagc gtcctctgtc cctgctgctg tgtttgttca | 1320 |
| gctctttaag agttcacccc attcgatctt gtggctccta aagccaaggg tgaaagtttg | 1380 |
| atccttgcag aggccactta aattcagaga acaaaaagca ccattctctg ccctagactc | 1440 |
| tagcccagat ccctgccagg tgtctgcctt ctggtcaaaa tgagacgctg gcaaaggggt | 1500 |
| gctagcctgt gacagtatgg gaacgcaaca aaggacaccc ctctacatgc gacttgctct | 1560 |
| ttgtgtgctc acgggacctg acatcattca cagagaacac agattgcact ttactgtcag | 1620 |
| ccctggaagt ctgagtcaaa ctgaaataat gctccagcgc tacttacaaa aatccattat | 1680 |
| ctactcggcc taagtacaga gcctggcctc ctcgctgaca ggattctgtt ggcaatcaaa | 1740 |
| aaaaaaaaaa aaaaaaagca acactcagtc tttagtctgt atctctgtaa tagaaaatag | 1800 |
| caatacttat aagctgaaat caagcacagg ttttatgtta gtcaaagcca ttaagctatc | 1860 |
| aaaagtaaac ccatgtacac agaaacgtcc caggactggt ttgtaatatg tcctgacaaa | 1920 |
| taagccatga aaacaagctc ctcaaattac tgatgcaact ttttagcagg gtcacaaact | 1980 |
| cagctttctt taaattaagt cagctcttcc tagttttttac ttctctaatt acccagcact | 2040 |
| taacgcatat ttttcccctc aaatattagt tttagtaaca aaacagcact ccaagtctca | 2100 |
| aaggattaac attttctatt ttaaacacaa aatctaaatt aaaaattact aacttaaatg | 2160 |
| atagcaagag ttttacagag attaataagc tttaagtaca gtttatatta gtacacagac | 2220 |
| ttcaatttat caaatgtcac atatatcttt catgatttgg ggatttattt catttatgaa | 2280 |
| gtagtcaaat gaatcagctt gccctcgact gtaacaaaat gctgcttggt gacttgtgac | 2340 |
| agacagggtt ttaacctctg acagcgagat tcattgtgga gcaggagcca atcatagatc | 2400 |
| ctgacgacac ttgtctcctc taagttggaa tataaaagc cacttggaat acagtataca | 2460 |
| ggactccctg gcgtggcagg tt | 2482 |

<210> SEQ ID NO 2
<211> LENGTH: 1537
<212> TYPE: DNA
<213> ORGANISM: Sus scrofa

<400> SEQUENCE: 2

| | |
|---|---|
| ttgtggctcc taaagctaag gttgagagtt tgagctctac agaggccact taaatttaga | 60 |
| gaacaaaaag ctctattctc tgctcccaga ccttacccca aatccctgcc aggtgtctgc | 120 |
| cctctggtca aatgagaaac tggcaaaggg gtgcaaacct agcacagaat gggaaacag | 180 |
| aaaaatgggc acccttttatt atggtgctcc ttctcttttta tgtgtttaca atacttgggc | 240 |
| ataatttaca gagaatagat actacatttt ttactttcac cactggaaat ctgagggcaa | 300 |
| actgcattat cagtcataaa attcattatc tttctattct aagttattct aagcttattc | 360 |
| taagctcaga tagcagcata aacaggtaaa tataaacata gatttgcagt ttttgcatga | 420 |
| ttttaaaatc aatacaatct ttctccttgt tcttatttct tccttttact tttgcttttg | 480 |
| agtaacgcca agcaaaattt taatgcctgc actgtctgag agacaacttg ccacaccagt | 540 |
| gaatctttta tactgtattc caagtggctt tttatattcc acttgatgag acaagtgtcg | 600 |
| tcaggatcta tagttggctc ttgctccaca atgaatctcg ctgtcagagg ttaaaaccct | 660 |
| gtctgtcaca agtcaccaaa cagtatttttg ttacagtcaa gggtgagctg attcatttga | 720 |
| ctacttcata aaagaaataa atctacaaat aatgaaactg acattatcct cttggtaata | 780 |
| aacaatgaaa aaacacatct tctgagcaat attaatctgc aactttagga taggagaaaa | 840 |

```
tcagttgaaa actgagcacg attttcacgt gaataaaaga tattatttaa aaataattcc      900
atgtgtaata taacagaata agtatgattt tcattatgta ctagaaattt agtcaggaaa      960
acaagtttct caaattatag ctgaatatat tttactagta tcacaatctt aaattttaat     1020
tcaggtcttc ctaatttaaa tctgtatttc tctgattaca caggactaaa ataatttaa      1080
aacagcaaat aaaattcttt tttcctcaaa tgtttgtcta aataatgtaa aatcatttta     1140
ttttttgag gaaaaagaca tttcaacttt ttaagtatga agtgtaaaag aattacttat      1200
ttaaattaca attttaaagt ttcactaata aagattaata atatttaagt gcagtttata     1260
ttattgttaa catagatttt aatttttcaa atgtcacata tatctttcat tatttgtaga     1320
tttatttctt ttatgaagta gtcaaatgaa tcagctcacc cttgactgta acaaaatact     1380
gtttggtgac ttgtgacaga cagggtttta acctctgaca gcgagattca ttgtggagca     1440
agagccaact atagatcctg acgacacttg tctcatcaag tggaatataa aaagccactt     1500
ggaatacagt ataaaagatt cactggtgtg gcaagtt                              1537

<210> SEQ ID NO 3
<211> LENGTH: 200
<212> TYPE: DNA
<213> ORGANISM: Mus musculus

<400> SEQUENCE: 3
agtcaaatga atcagcttgc cctcgactgt aacaaaatgc tgcttggtga cttgtgacag       60
acagggtttt aacctctgac agcgagattc attgtggagc aggagccaat catagatcct      120
gacgacactt gtctcctcta agttggaata taaaaagcca cttggaatac agtatacagg      180
actccctggc gtggcaggtt                                                  200

<210> SEQ ID NO 4
<211> LENGTH: 20
<212> TYPE: DNA
<213> ORGANISM: artificial sequence
<220> FEATURE:
<221> NAME/KEY: Artificial sequence
<222> LOCATION: (1)..(20)
<223> OTHER INFORMATION: primer

<400> SEQUENCE: 4
actgggccag cagcaatcag                                                   20

<210> SEQ ID NO 5
<211> LENGTH: 20
<212> TYPE: DNA
<213> ORGANISM: artificial sequence
<220> FEATURE:
<221> NAME/KEY: Artificial sequence
<222> LOCATION: (1)..(20)
<223> OTHER INFORMATION: primer

<400> SEQUENCE: 5
gagtaatgcc aagtgaaata                                                   20

<210> SEQ ID NO 6
<211> LENGTH: 29
<212> TYPE: DNA
<213> ORGANISM: artificial sequence
<220> FEATURE:
<221> NAME/KEY: Artificial sequence
<222> LOCATION: (1)..(29)
<223> OTHER INFORMATION: primer
```

```
<400> SEQUENCE: 6
gcagacaccc tgaggtgatc tggccctct                                              29

<210> SEQ ID NO 7
<211> LENGTH: 28
<212> TYPE: DNA
<213> ORGANISM: artificial sequence
<220> FEATURE:
<221> NAME/KEY: Artificial sequence
<222> LOCATION: (1)..(28)
<223> OTHER INFORMATION: primer

<400> SEQUENCE: 7
ttttctgcat agaattcttt tcgatgtc                                               28

<210> SEQ ID NO 8
<211> LENGTH: 22
<212> TYPE: DNA
<213> ORGANISM: artificial sequence
<220> FEATURE:
<221> NAME/KEY: Artificial sequence
<222> LOCATION: (1)..(22)
<223> OTHER INFORMATION: primer

<400> SEQUENCE: 8
gtaatacgac tcactatagg gc                                                     22

<210> SEQ ID NO 9
<211> LENGTH: 19
<212> TYPE: DNA
<213> ORGANISM: Artificial Sequence
<220> FEATURE:
<221> NAME/KEY: Artificial sequence
<222> LOCATION: (1)..(19)
<223> OTHER INFORMATION: primer

<400> SEQUENCE: 9
actatagggc acgcgtggt                                                         19
```